United States Patent [19]

Rolf et al.

[11] Patent Number: 4,666,526
[45] Date of Patent: May 19, 1987

[54] AZINE PIGMENTS, PROCESSES FOR THEIR PREPARATION, AND THEIR USE

[75] Inventors: Meinhard Rolf; Rütger Neeff, both of Leverkusen, Fed. Rep. of Germany

[73] Assignee: Bayer Aktiengesellschaft, Leverkusen, Fed. Rep. of Germany

[21] Appl. No.: 691,990

[22] Filed: Jan. 16, 1985

[30] Foreign Application Priority Data

Jan. 18, 1984 [DE] Fed. Rep. of Germany ....... 3401574

[51] Int. Cl.[4] ..................... C09B 67/20; C07D 519/00
[52] U.S. Cl. .................................... 106/309; 544/245; 544/246; 106/288 Q; 106/308 Q
[58] Field of Search ............................. 544/245, 246; 106/288 Q, 308 Q, 309

[56] References Cited

U.S. PATENT DOCUMENTS 4,564,680 1/1986 Rolf et al. .................... 106/288 Q X

OTHER PUBLICATIONS

Gabriel, Berichte, vol. 45, pp. 713-725 (1912).
Peterson, et al., Chemical Abstracts, vol. 54, 14257i--14258g (1960).
Siling, et al., Izv. Akad. Nauk SSSR, Ser. Khim. 1978 (8), pp. 1871-1877 (1978).
Ponomarev, et al., Chemical Abstracts, vol. 94, 103320z (1981).
Baumann, et al., Angewandte Chemie, vol. 68, No. 4, pp. 133-150 (1956).

Primary Examiner—Robert Gerstl
Assistant Examiner—Diana G. Rivers
Attorney, Agent, or Firm—Sprung Horn Kramer & Woods

[57] ABSTRACT

Azine pigments having the probable structure

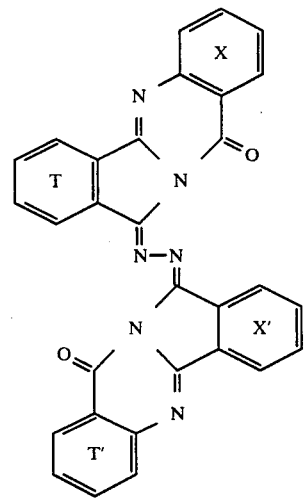

(I)

wherein the rings designated by T, R', X and X' can be substituted or expanded to naphthalene systems. The pigments can be prepared by reacting compounds having the probable structures

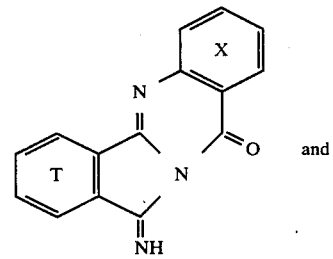

(IV)

and

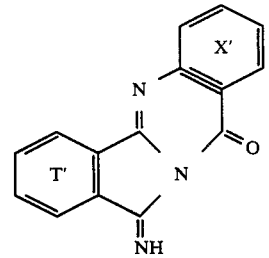

(IVa)

in the presence of hydrazine. The compounds having the probable structures (IV) and (IVa) are formed by reacting isatoic anhydrides or anthranilic acid esters or anthranilic acid amides with at least one mol of an aminoiminoisoindolenine.

14 Claims, No Drawings

AZINE PIGMENTS, PROCESSES FOR THEIR PREPARATION, AND THEIR USE

The invention relates to azine pigments having the probable structure

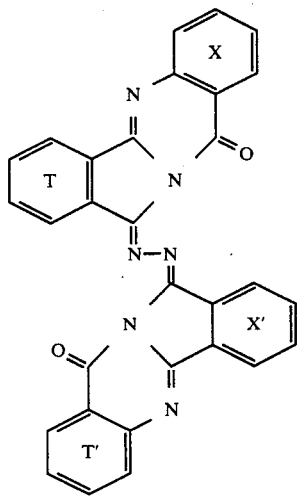
(I)

processes for their preparatin, and their use.

In formula (I), the rings designated by X, X', T and T' can be substituted, for example in each case by 1, 2, 3 or 4 substituents from the series comprising halogen, in particular chlorine and bromine; $C_1$–$C_6$-alkyl, in particular methyl; aryl, in particular phenyl, which in turn can be substituted by halogen, such as chlorine and bromine, $C_1$–$C_6$-alkyl, such as methyl, acylamino, such as acetylamino or benzylamino, nitro, carboxyl or carbamoyl; $C_1$–$C_6$-alkoxy, in particular methoxy; acylamino, in particular acetylamino and benzoylamino; carboxyl; nitro or cabamoyl. The rings X, X', T and T' can furthermore be expanded by means of fused benzo rings, which may be substituted, to give naphthalene systems. Suitable substituents in the naphthalene rings are halogen, such as chlorine and bromine, $C_1$–$C_6$-alkyl, such as methyl, acylamino, such as acetylamino or benzylamino, nitro, carboxyl or carbamoyl.

Symmetric azine pigments having the probable formula

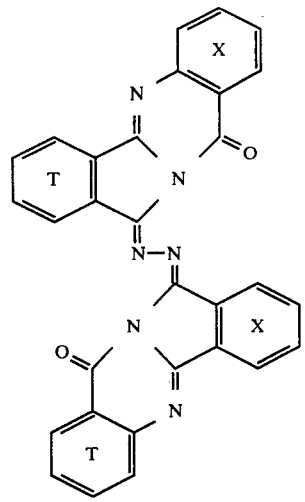
(II)

in which the rings denoted by X and/or the rings denoted by T are substituted by 1, 2, 3 or 4 chlorine or bromine atoms, are preferred. Other preferred symmetric azine pigments of the probable formula (II) are those in which the rings denoted by X and/or the rings denoted by T carry a substitute from the series comprising methyl, methoxy, acetylamino, benzoylamino, carboxyl, carbamoyl and nitro.

The symmetric azine pigment of the probable formula

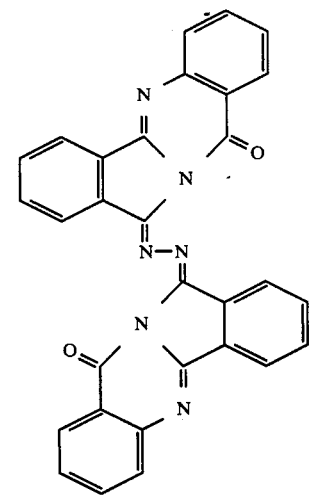
(III)

is also preferred.

The new azine pigments of the probable formula (I) can be obtained by a method in which a compound of the probable formula

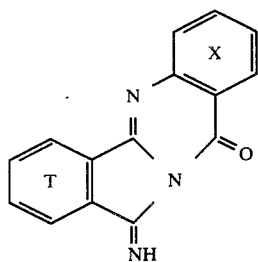
(IV)

is reacted with a compound of the probable formula

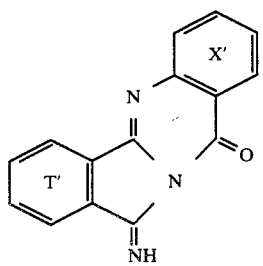
(IVa)

in the presence of hydrazine or of a hydrazine-donating compound, such as hydrazine hydrate or a hydrazinium salt. In the formulae (IV) and (IVa), T, T', X and X' have the meanings given for formula (I).

In this procedure, the reaction is advantageously carried out in water or in an organic solvent under slightly acidic conditions and at elevated temperature, preferably at 50°–180° C. Suitable organic solvents are alcohols, such as methanol, ethanol, amyl alcohol or glycol monoalkyl ethers; aromatics, such as chlorobenzene, nitrobenzene or toluene; amide solvents, such as formamide, dimethylformamide or N-methylpyrrolidone; or acids, such as formic acid or acetic acid.

Suitable acids for establishing the acid conditions are inorganic acids, such as hydrochloric acid, sulphuric acid or phosphoric acid, and organic acids, such as formic acid, acetic acid, chloroacetic acid, dichloroacetic acid, oxalic acid, benzenesulphonic acid or p-toluenesulphonic acid.

Instead of the intermediate products of the formulae (IV) and (IVa), it is also possible to use their acylation products of the probable formulae (V) and (Va):

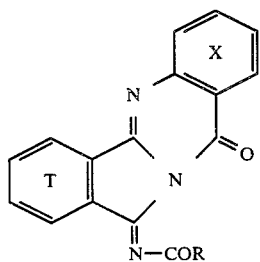
(V)

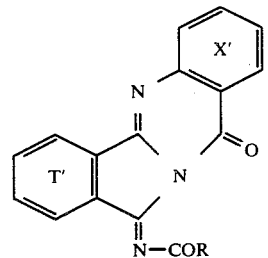
(Va)

In the formulae (V) and (Va), T, T', X and X' have the meanings given for formula (I); R designates alkyl, preferably $C_1$–$C_6$-alkyl, in particular methyl, or aryl, in particular phenyl.

The compounds of the probable formula (IV) are obtainable by reacting an isatoic anhydride of the formula (VI)

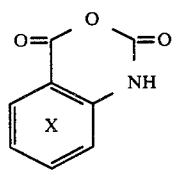
(VI)

or an anthranilic acid ester or anthranilic acid amide of the formula (VII)

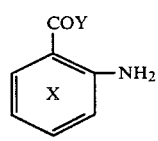
(VII)

with at least one mol of an aminoiminoisoindolenine of the formula

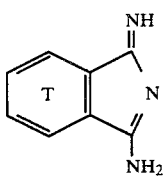
(VIII)

in an inert organic solvent, for example ethanol, at elevated temperature, preferably at 50°–100° C.

In the formulae (VI), (VII) and (VIII), T and X have the meanings given for formula (I).

In formula (VII), Y designates —$NH_2$ or —OR', wherein R' represents the hydrocarbon radical of an ester, preferably $C_1$–$C_6$-alkyl.

The intermediate products of the probable formula (IVa) are obtained by a very similar method.

Compounds which can be employed according to the invention and which have been assigned the formulae (IV) and (IVa) are known from the literature (Angew. Chem. 68, 135 (1956)).

Another method of preparation for the pigments of the probable formula (I) comprises the condensation of a hydrazone of the probable formula

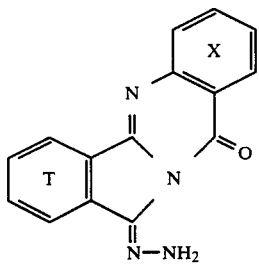

(IX)

with a hydrazone of the probable formula

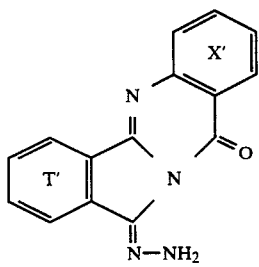

(IXa)

in an acidic medium, the pigments of the probable formula (I) being formed with elimination of one mol of hydrazine. This reaction is advantageously carried out in organic solvents at elevated temperature, preferably at 50°–180° C. The solvents which are preferably used and the acids preferably employed to obtain the acidic medium correspond to those stated for the reaction of the compounds of the probable formulae (IV) and (IVa).

In the formulae (IX) and (IXa), T, T', X and X' having the meanings given for formula (I).

The compounds of the probable formulae (IV) and (IVa) or (V) and (Va) or (IX) and (IXa) can be reacted in any desired ratio. Preferably, they are identical compounds which react to give the symmetric azine pigments of the probable formula (II).

The compounds of the probable formula (I) are obtained in the form suitable for use as pigments, or can be converted to the suitable form by after-treatment methods which are known per se, for example by dissolution or swelling in strong inorganic acids, such as sulphuric acid, and pouring onto ice. A finely divided material can also be obtained by milling with or without milling auxiliaries, such as inorganic salts or sand, if appropriate in the presence of solvents, such as toluene, xylene, dichlorobenzene or N-methylpyrrolidone. The tinctorial strength and the transparency of the pigment can be influenced by varying the after-treatment.

Because of their fastness to light and to migration, the colorants of the probable formula (I) are suitable for a large variety of pigment applications. They can be used for the preparation of very fast pigmented systems, such as mixtures with other substances, formulations, paints, printing inks, coloured paper and coloured macromolecular substances. Mixtures with other substances can be understood as meaning, for example, those with inorganic white pigments, such as titanium dioxide (rutile) or with cement. Examples of formulations are flushed colours containing organic liquids or pastes and fine pastes containing water, dispersants and, if appropriate, preservatives. The term paint represents, for example, physically or oxidatively drying lacquers, stoving enamels, reaction lacquers, two-component lacquers, dispersion paints for weather-resistant coatings and distempers. Printing inks are understood as meaning those which are used for paper printing, textile printing and tin printing.

The macromolecular substances can be of natural origin, such as rubber, can be obtained by chemical modification, such as acetyl cellulose, cellulose butyrate or viscose, or can be produced synthetically, such as polymers, polyadducts and polycondensates. Plastic materials, such as polyvinyl chloride, polyvinyl acetate, polyvinyl propionate, polyolefins, for example polyethylene or polyamides, superpolyamides, polymers and copolymers of acrylates, methacrylates, acrylonitrile, acrylamide, butadiene and styrene, and polyurethanes and polycarbonates, may be mentioned. The substances pigmented with the claimed products can be in any desired form.

The pigments of the probable formula (I) also possess excellent water-fastness, oil-fastness, acid-fastness, lime-fastness, alkali-fastness, fastness to solvents, fastness to overcoating, fastness to overspraying, fastness to sublimation, heat-resistance and resistance to vulcanisation, have a very high colour yield and can readily be distributed in plastic materials.

It should be pointed out that the structural formulae given in the examples below are probable structural formulae.

EXAMPLE 1

(a) 5.5 g of hydrazine hydrate are added, at 110° C., to 50 g of the reaction product of aminoimino-isoindolenine with isatoic anhydride, in a mixture of 500 ml of nitrobenzene and 20 ml of glacial acetic acid. Stirring is continued for 5 hours at 110° C. and for 3 hours at 150° C., the product is filtered off under suction from the hot mixture, and 26 g of a yellow pigment of the formula

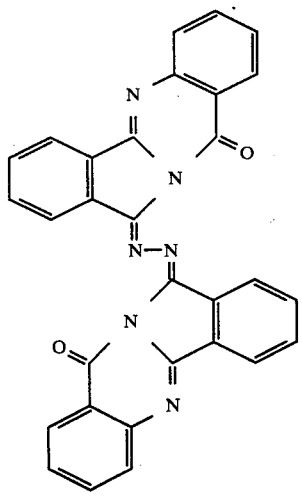

are obtained.

Melting point: 360° C.

Mass spectrum m/e (relative intensity): 492 $M^+$ (100%), 404 (54), 435 (15), 219 (30), 204 (50), 90 (60), 76 (45).

Ir spectrum ($cm^{-1}$): 3400, 1700, 1640, 1580, 1450, 1320, 1240, 1120, 930, 760, 690.

(b) 10 g of the hydrazone of the formula

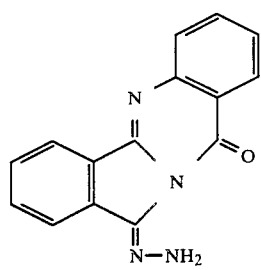

are introduced into a mixture of 100 ml of dimethylformamide and 5 ml of 96% strength sulphuric acid, and the mixture is stirred for 30 minutes at 130° C. After the product has been filtered off under suction and dried, this procedure gives 4 g of a yellow pigment which is identical to that obtained according to Example 1a.

TABLE

Examples 2-16
When substituted starting materials are used, corresponding azine pigments having the shades given in the table are obtained analogously to Example 1a:

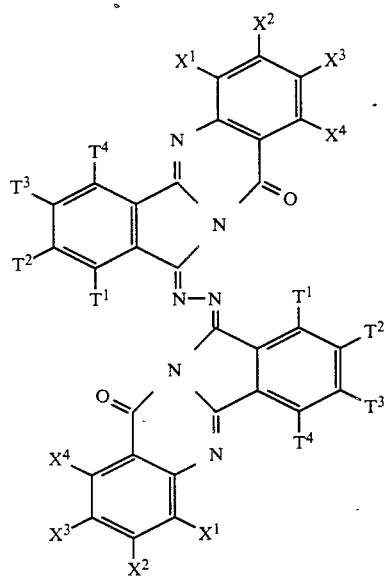

| Example | $T^1$ | $T^2$ | $T^3$ | $T^4$ | $X^1$ | $X^2$ | $X^3$ | $X^4$ | Shade |
|---|---|---|---|---|---|---|---|---|---|
| 2 | H | $C_6H_5$ | H | H | H | H | H | H | reddish yellow |
| 3 | Cl | Cl | Cl | Cl | H | H | H | H | orange |
| 4 | H | H | H | H | H | Cl | H | H | greenish yellow |
| 5 | H | H | H | H | H | H | Cl | H | greenish yellow |
| 6 | H | H | H | H | H | H | H | Cl | greenish yellow |
| 7 | H | H | H | H | Cl | H | Cl | H | greenish yellow |
| 8 | H | H | H | H | Br | H | Br | H | yellow |
| 9 | H | H | H | H | Cl | Cl | Cl | Cl | greenish yellow |

| Example | $T^1$ | $T^2$ | $T^3$ | $T^4$ | $X^1$ | $X^2$ | $X^3$ | $X^3$ | Shade |
|---|---|---|---|---|---|---|---|---|---|
| 10 | H | H | H | H | H | $NO_2$ | H | H | yellow |
| 11 | H | H | H | H | H | H | $NO_2$ | H | yellow |
| 12 | H | H | H | H | H | $NHCOCH_3$ | H | H | yellow |
| 13 | H | H | H | H | H | $CH_3$ | H | H | yellow |

TABLE-continued

Examples 2-16
When substituted starting materials are used, corresponding azine pigments having the shades given in the table are obtained analogously to Example 1a:

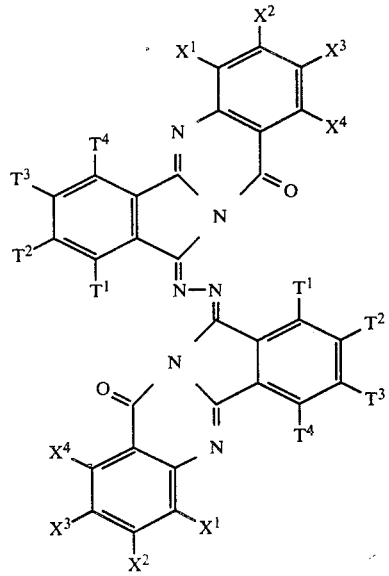

| 14 | H | H | H | H | H | $OCH_3$ | H | H | orange |
|---|---|---|---|---|---|---|---|---|---|
| 15 | H | H | H | H | H | $CONH_2$ | H | H | yellow |
| 16 | Cl | Cl | Cl | Cl | Cl | Cl | Cl | Cl | orange |

EXAMPLE 17

When a mixture of 5 g of (X) and 7.8 g of (XI) is reacted analogously to Example 1a, a yellow azine pigment is obtained

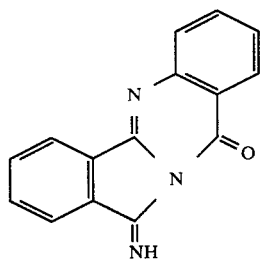 (X)

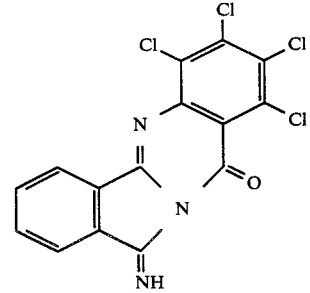 (XI)

in which the two components (X) and (XI) are present as a mixture.

EXAMPLES 18-19

When the intermediate products (XII) and (XIII)

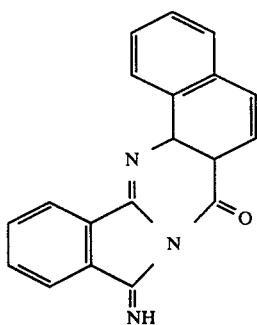

(XII)

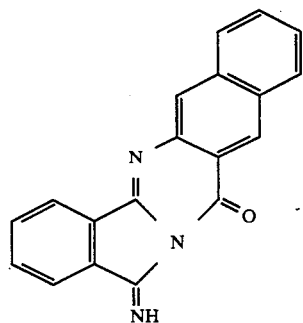

(XIII)

are employed analogously to Example 1a, the corresponding dimeric azine pigments are obtained, these pigments giving brown shades.

EXAMPLE 20 (USE EXAMPLE)

8 g of finely milled pigment according to Example 1a are dispersed in 92 g of a stoving enamel having the following composition:

33% of alkyd resin
15% of melamine resin
5% of glycol monomethyl ether
34% of xylene
13% of butanol Suitable alkyd resins are produces based on synthetic and vegetable fatty acids, such as coconut oil, castor oil, dehydrated castor oil, linseed oil and others. Instead of melamine resins, it is also possible to use urea resins.

When dispersing is complete, the pigmented lacquer is applied onto paper sheets, glass sheets, plastic films or metal foils and baked for 30 minutes at 130° C. The coatings possess very good light-fastness and weather-resistance as well as good fastness to overcoating.

EXAMPLE 21 (USE EXAMPLE)

0.2 g of the pigment according to Example 1a is mixed with 100 g of polyethylene granules, polypropylene granules or polystyrene granules. The mixture can be either injection moulded directly in an injection moulding machine at 220° to 280° C., or processed in an extruder to give coloured bars, or on a roll mill to give coloured hides. If required, the bars or hides are granulated, and the granules injection moulded in an injection moulding machine.

The yellow mouldings possess very good light-fastness and fastness to migration. Synthetic polyamides obtained from caprolactam or adipic acid and hexamethylenediamine or the condensates obtained from terephthalic acid and ethylene glcyol can be coloured in a similar manner at 280°–300° C., if appropriate under a nitrogen atmosphere.

EXAMPLE 22 (USE EXAMPLE)

Yellow offset prints of high brilliance and intensity and having very good light-fastness and fastness to lacquering are obtained using a printing ink prepared by milling 35 g of the pigment according to Example 1a and 65 g of linseed oil and adding 1 g of a siccative (Co naphthenate, 50% strength in mineral spirit). When these printing inks are used in letterpress printing, collotype printing, lithographic printing or die stamping, yellow prints having similar fastness properties are obtained. If the pigment is used for colouring tin printing inks or low-viscosity gravure printing inks, orange-coloured prints having similar fastness properties are obtained.

We claim:

1. An azine pigment of the structure

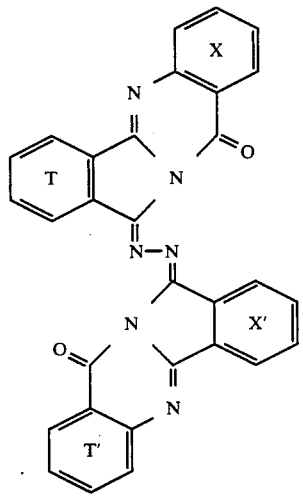

(I)

wherein the rings designated T, T', X and X' are unsubstituted or substituted in each case by 1, 2, 3 or 4 substituents selected from the group consisting of halogen; $C_1$-$C_6$-alkyl; unsubstituted phenyl or phenyl substituted by halogen, $C_1$-$C_6$-alkyl, acetylamino, benzoylamino, nitro, carboxyl or carbamoyl; $C_1$-$C_6$-alkoxy acetylamino; benzoylamino; carboxyl; nitro or carbamoyl; or the rings X, X', T and T' are expanded to naphthalene systems by means of fused benzo rings, and the naphthalene rings being unsubstituted or substituted by halogen, $C_1$-$C_6$-alkyl, acetylamino, benzoylamino, nitro, carboxyl or carbamoyl.

2. A symmetric azine pigment of the formula

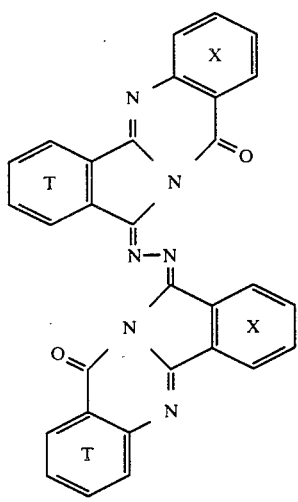

in which the rings denoted by X and/or the rings denoted by T are substituted by 1, 2, 3 or 4 chlorine or bromine atoms.

3. A symmetric azine pigment according to claim 1, in which the rings denoted by X and/or the rings denoted by T carry a substituent selected from the group consisting of methyl, methoxy, acetylamino, benzoylamino, carboxyl, carbamoyl and nitro.

4. An azine pigment of the formula

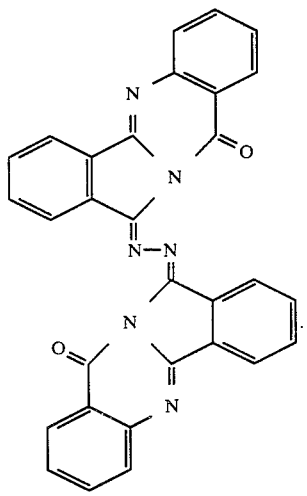

5. An azine pigment according to claim 1, which is obtained when a compound of the formula

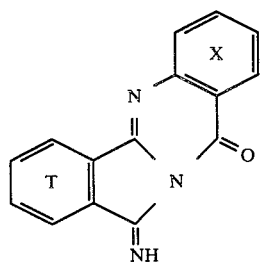

is reacted with a compound of the formula

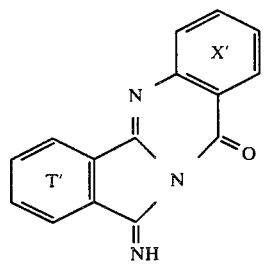

wherein
T, T', X and X' have the meanings given in claim 1, in the presence of hydrazine hydrate or a hydrazinium salt.

6. An azine pigment according to claim 1, which is obtained when a compound of the formula

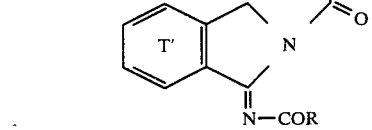

is reacted with a compound of the formula

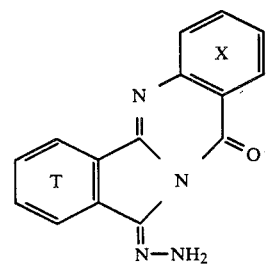

wherein
T, T', X and X' have the meaning given in claim 1 and R designates $C_1-C_6$-alkyl or phenyl, in the presence of hydrazine hydrate or a hydrazinium salt.

7. An azine pigment according to claim 1, which is obtained when a compound of the formula (II)

(III)

(IV)

(IVa)

(V)

(Va)

(IX)

is reacted with a compound of the formula

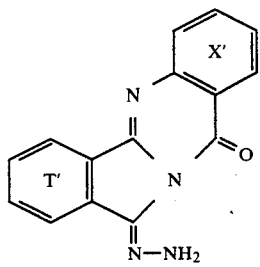
(IXa)

in an acidic medium with elimination of hydrazine.

8. An azine pigment according to claim 6, obtainable by a method in which the compounds of the formula

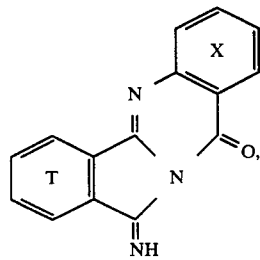
(IV)

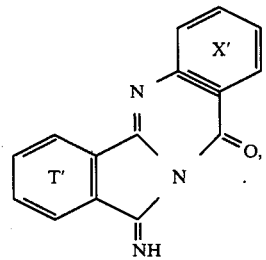
(IVa)

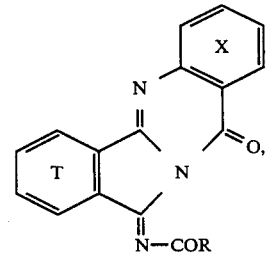
(V)

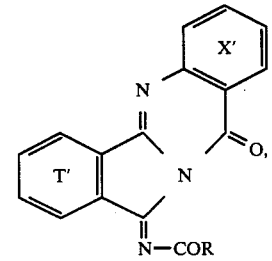
(Va)

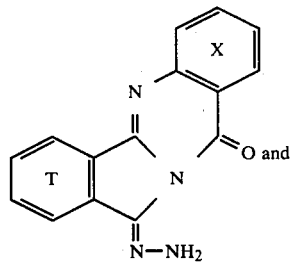
(IX)

and

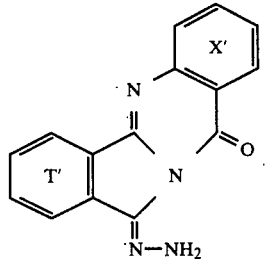
(IXa)

are prepared by reacting an isatoic anhydride of the formula

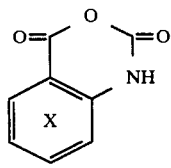
(VI)

or of the formula

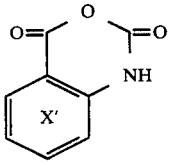
(VIa)

or an anthranilic acid amide or anthranilic acid ester of the formula

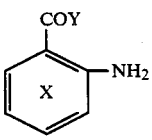
(VII)

or of the formula

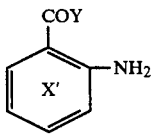
(VIIa)

wherein
the rings X and X' are unsubstituted or substituted by 1, 2, 3 or 4 substituents selected from the group consisting of halogen; $C_1$-$C_6$-alkyl; unsubstituted phenyl or phenyl substituted by $C_1$-$C_6$-alkyl, halogen, acetylamino, benzoylamino, nitro, carboxyl or carbamoyl; $C_1$-$C_6$-alkoxy; acetylamino; benzoylamino; carboxyl; nitro or carbamoyl, or the rings are expanded to naphthalene systems by means of fused benzo rings, and the naphthalene rings are unsubstituted or substituted by halogen, $C_1$-$C_6$-alkyl, acetylamino, benzoylamino, nitro, carboxyl or carbamoyl, and Y designates —$NH_2$ or —OR', and R' represents $C_1$-$C_6$-alkyl with at least one mol of a compound of the formula

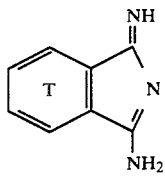

(VIII)

or of the formula

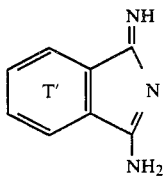

(VIIIa)

wherein the rings T and T' are unsubstituted or substituted by 1, 2, 3 or 4 substituents selected from the group consisting of halogen; $C_1$-$C_6$-alkyl; unsubustituted phenyl or phenyl substituted by halogen, $C_1$-$C_6$-alkyl, acetylamino, benzoylamino, nitro, carboxyl or carbamoyl; $C_1$-$C_6$-alkoxy; acetylaino; benzoylamino; carboxyl; nitro or carbamoyl, or the rings being expanded to naphthalene systems by means of fused benzo rings, and the naphthalene rings being unsubstituted or substituted by halogen, $C_1$-$C_6$-alkyl, acetylamino, benzylamino, nitro, carboxyl or carbamoyl, in an inert organic solvent at elevated temperature with, if necessary, subsequent acylation or hydrazone formation.

9. In a process for pigmenting polymers, polyadducts and polycondensates including contacting a pigment with said polymers, polyadducts or polycondensates, the improvement comprising said pigment being an azine pigment according to claim 1.

10. An azine pigment according to claim 1, wherein said halogen is selected from the group consisting of chlorine and bromine.

11. An azine pigment according to claim 1, wherein said $C_1$-$C_6$-alkyl is methyl.

12. An azine pigment according to claim 1, wherein said $C_1$-$C_6$-alkoxy is methoxy.

13. An azine pigment according to claim 8, wherein said halogen is selected from the group consisting of chlorine and bromine.

14. An azine pigment according to claim 8, wherein said $C_1$-$C_6$-alkyl is methyl.

* * * * *